United States Patent

Breuer

[11] B 3,984,404
[45] Oct. 5, 1976

[54] ACYLTHIOMETHYL ESTERS OF CEPHALOSPORINS

[75] Inventor: Hermann Breuer, Regensburg, Germany

[73] Assignee: E. R. Squibb & Sons, Inc., Princeton, N.J.

[22] Filed: Oct. 21, 1974

[21] Appl. No.: 516,296

[44] Published under the second Trial Voluntary Protest Program on February 3, 1976 as document No. B 516,296.

Related U.S. Application Data

[63] Continuation-in-part of Ser. No. 277,700, Aug. 3, 1972, Pat. No. 3,860,591.

[52] U.S. Cl. ............................ 260/243 C; 424/246
[51] Int. Cl.² ........................................ C07D 501/20
[58] Field of Search ............................... 260/243 C

[56] References Cited
UNITED STATES PATENTS

| | | |
|---|---|---|
| 3,847,913 | 11/1974 | Gudtfredsen et al. .......... 260/243 C |
| 3,852,282 | 12/1974 | Dolfini ............................ 260/243 C |
| 3,855,213 | 12/1974 | Dunn et al. ..................... 260/243 C |
| 3,867,380 | 2/1975 | Dunn et al. ..................... 260/243 C |

Primary Examiner—Nicholas S. Rizzo
Attorney, Agent, or Firm—Lawrence S. Levinson; Merle J. Smith

[57] ABSTRACT

New acylthiomethyl esters of cephalosporins have the formula

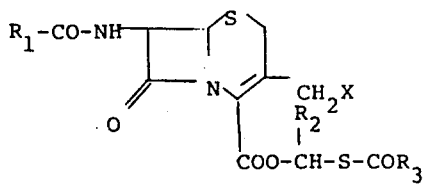

wherein $R_1$ is α-aminobenzyl; $R_2$ is hydrogen or lower alkyl; $R_3$ is lower alkyl; and X is tetrazolylthio or (lower alkyl)tetrazolylthio. They are useful as antibacterial agents.

6 Claims, No Drawings

ACYLTHIOMETHYL ESTERS OF CEPHALOSPORINS

This application is a continuation-in-part of application Ser. No. 277,700, filed Aug. 3, 1972, U.S. Pat. 3,860,591, issued Jan. 14, 1975.

BACKGROUND OF THE INVENTION

It is known that many cephalosporins are either not absorbed or not readily absorbed in the gastrointestinal tract, 7-(2-thienylacetamido)cephalosporanic acid, for example. Such compounds are usually administered parenterally in order to achieve high serum concentrations. It is therefore advantageous to have derivatives of cephalosporins a high percentage of which are absorbed on oral administration and produce their antiobiotic effect.

The new acylthiomethyl cephalosporin esters of this invention are more readily absorbed from the gastrointestinal tract and then are readily hydrolyzed to the free cephalosporin thereby providing a high concentration of antibiotically active substance.

SUMMARY OF THE INVENTION

This invention relates to new acylthiomethyl esters of cephalosporins having the formula (I)

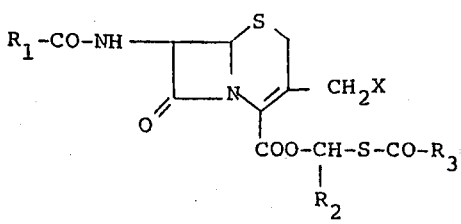

$R_1$ is hydrogen, lower alkyl, cycloalkylmethyl, like cyclo-propylmethyl, cyclobutylmethyl, cyclopentylmethyl or cyclo-hexylmethyl, cycloalkenylmethyl, monounsaturated cycloaliphatics like the foregoing cycloalkylmethyl groups, cycloalkadienylmethyl like cyclopentadienylmethyl or cyclohexadienylmethyl, aryloxy-methyl like phenoxymethyl, aralkyl, e.g., phenyl-lower alkyl or the same groups with simple substituents on the phenyl, cyano-methyl, azidomethyl, and certain heterocyclic groups like furylmethyl thienylmethyl, oxazolylmethyl, thiazolylmethyl, isoxazolylmethyl, oxadiazolylmethyl, thiadiazolylmethyl, tetrazolylmethyl, pyridylthio-methyl, and such groups simply substituted. Members of the foregoing groups substituted on the α-carbon atom with an amino, hydroxy, carboxy, ureido, lower alkanoylureido, sulfonylureido, sulfonyl or sulfonylamido groups are also included. $R_2$ is hydrogen, lower alkyl, phenyl or phenyl-lower alkyl. $R_3$ represents lower alkyl, lower alkenyl, aryl, halophenyl, benzhydryl or aralkyl groups such as those described above. X is hydrogen, hydroxy, lower alkanoyloxy, aroyloxy, lower alkoxy, aralkanoyloxy, the radical of a nitrogen base such as alkylamines or aralkylamines, quaternary ammonium radicals like pyridinium, quinolinium, picolinium and the like, lower alkylthio, certain heterocyclic substituted mercapto groups like oxazolylthio, thiadiazolylthio, thiatrizolylthio or lower alkyl substituted members of this group.

When $R_1$ is a basic substituent the products form acid addition salts which are also within the scope of the invention.

The preferred members of the group are those wherein $R_1$ is benzyl, phenoxymethyl, α-substituted benzyl, especially wherein the α-substituent is amino, hydroxy, carboxy or ureido, thienylmethyl, and α-substituted thienylmethyl especially wherein the α-substituent is amino, hydroxy, carboxy or ureido, pyridylthiomethyl, azidomethyl or cyanomethyl, $R_2$ is hydrogen, lower alkyl, especially methyl, phenyl or phenyl-lower alkyl, especially benzyl, $R_3$ is lower alkyl, especially methyl, ethyl, propyl, N-butyl, t-butyl or 1,1-diethylpropyl, lower alkeny especially allyl, phenyl, chlorophenyl, phenyl-lower alkyl, especially benzyl, phenethyl or α-methylbenzyl, or benzhydryl, and X is hydrogen lower alkanoyloxy, especially acetoxy or propionyloxy, benzoyloxy, pyridinium, lower alkoxy, especially methoxy, lower alkylthio, especially methylthio, thiatriazolylthio, thiadiazo lylthio, oxazolylthio and the lower alkyl, especially methyl, substituted members of the last two.

DETAILED DESCRIPTION OF THE INVENTION

The various groups represented by the symbols have the meanings defined below and these definitions are retained throughout this specification.

The lower alkyl groups are straight or branched chain hydrocarbon radicals having one to eight carbons in the chain, for example, methyl, ethyl, propyl, isopropyl, butyl, isobutyl, s-butyl, t-butyl, amyl or the like. The lower alkenyl groups are monounsaturated groups like those first described, the two to four carbon members being preferred.

The aryl groups are monocyclic carbocyclic aryl groups including simply substituted members. By way of illustration, this includes the phenyl ring and simply substituted phenyl containing one to three substituents (preferably only one) such as the halogens (chlorine and bromine being preferred), lower alkyl groups such as those defined above, lower alkoxy groups, (i.e., lower alkyl groups of the type defined above attached to an oxygen), hydroxy, amino, carboxy and the like. In the case of the last two named substituents there is preferably only one, especially in the para position of the phenyl.

The aralkyl groups include a monocyclic carbocyclic aryl group attached to a lower alkyl group, both as defined above, benzyl being preferred.

The cylo-lower alkyl groups are the alicyclics of three to six carbon atoms, e.g., cyclopropyl, cyclobutyl, cyclopentyl and cyclohexyl; cyclopentyl and cyclohexyl are preferred. The cyclo-lower alkenyl groups are the 4 to 6 carbons monounsaturated cyclic groups including cyclobutene, cyclopentene and cyclohexene. The cyclo-lower alkadiene groups are similar cyclic groups which have two double bonds, particularly cyclohexadienyl and especially 1,4-cyclohexa-dienyl, All of these are attached to a bridging methylene group.

The heterocyclic groups represented by $R_1$ are the heterocyclic radicals thienylmethyl, furylmethyl, oxazolylmethyl, isoxazolylmethyl, oxadiazolylmethyl, thiadiazolylmethyl, tetra-zolylmethyl and thiazolylmethyl, as well as these heterocyclics with the substituents halo, lower alkyl (particularly methyl and ethyl), lower alkoxy (particularly methoxy and ethoxy) or phenyl, and thienylmethyl having amino, hydroxy, carboxy or ureido as an α-substituent.

In addition, the $R_1$ groups, especially those with a cyclic substituent, may be substituted on the α-carbon atom. These include hydroxy, amino, carboxy, ureido, lower alkanoylureido, sulfonylureido, sulfonyl or sulfonylamido.

The lower alkanoyloxy, aroyloxy and aralkanoyloxy groups represented by X include the acyl group of acid esters. The lower alkanoyl radicals are the acyl radicals of lower fatty acids containing alkyl radicals of the type described above. The lower alkanoyloxy groups include, for example, acetoxy, propionyloxy, butyryloxy and the like. The aroyloxy groups are derived from monocyclic carbocyclic aryl groups of the kind described. Similarly the aralkanoyloxy groups consist of monocyclic carbocyclic aryl and alkanoyloxy radicals of the type described. X also represents the radical of an amine, e.g., an alkylamine like methylamine, ethylamine, dimethylamine, triethylamine, aralkylamine like dibenzylamine, N,N'-dibenzyl-pyridinium, pyridinium, 1-quinolinium, 1-picolinium, etc. The lower alkylmercapto groups represented by X include, for example, methylmercapto, ethylmercapto, propylmercapto and the like. The mercapto group may in addition bear one of the heterocyclic radicals oxadiazolyl, thiadiazolyl, tetrazolyl or thiatriazolyl, these heterocyclics may also bear a lower alkyl group, preferably methyl.

The compounds described above are essentially neutral, when $R_1$, however, is a basic group, α-aminobenzyl for example, acid addition salts of the conventional type are formed, e.g., hydrohalides like the hydrochloride, other inorganic acid salts like the sulfate, phosphate, organic salts like the citrate, benzenesulfonate, toluenesulfonate, etc.

The new compounds of this invention may be synthesized by several methods.

According to one method the carboxy group of a cephalosporin of the formula (II)

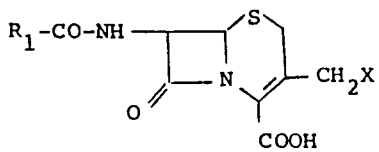

is first converted to an activated derivative. This activated derivative is preferably formed by treatment with dicyclo-hexylcarbodiimide, but may also be the reaction product with an anhydride forming agent such as ethylchloroformate, benzoyl chloride, pivaloyl chloride, etc., or with bis-imidazolecarbonyl, p-nitrophenol and the like. The activated derivative of the compound of formula II is made to react with an acylmercaptomethanol derivative of the formula (III)

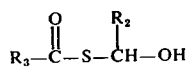

This reaction is effected at a temperature in the range of about 0°C. to ambient temperature in an inert organic solvent such as tetrahydrofuran, dimethylformamide, dimethylacetamide, acetone, dioxane or the like and a product of formula I results.

Alternatively, a salt of a cephalosporin of the formula (IV)

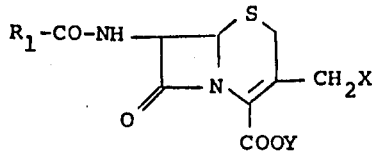

is made to react with a compound of the formula (V)

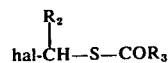

$R_1$, $R_2$, $R_3$ and X have the same meaning as above, Y is a cation, e.g., a metal cation such as the alkali metal cations sodium and potassium, or the cation of a nitrogen base such as the ammonium ion, trialkylammonium ions, etc., and hal is a halogen, especially chlorine or bromine.

This reaction is effected at a temperature of about 0° to 50°C., preferably in a suitable inert organic solvent such as dimethylformamide, dimethylacetamide, acetone, dioxane or the like.

The compounds of formulas III and V are produced by known methods [H. Bohme et al., Liebigs Annalen 623, 92–102 (1959)], for example, as shown in the following flow scheme, by reacting a thioacid of formula VI with an aldehyde of formula VII whereby the corresponding hydroxymethyl ester of the thioacid III is formed, this is halogenated, for example by treatment with a phosphorus trihalide, like phosphorus tribromide, to obtain the corresponding halomethyl ester (V):

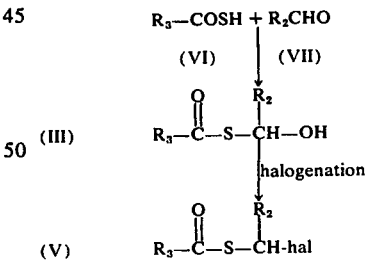

The synthesis of the new acylthiomethyl esters of penicillins of formula I may also be effected from α-haloalkyl esters of cephalosporanic acid derivatives of the formula (VIII)

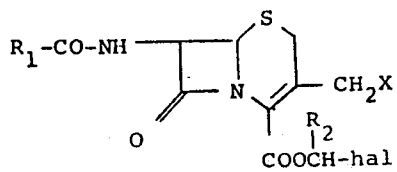

The compound of formula VIII is reacted with a salt, for example, an alkali metal salt, of a compound of formula VI above in an inert organic solvent, such as those named previously, at a temperature of about 0° to 50°C., preferably at room temperature.

The compounds of formula I may also be produced by acylating a compound of the formula (IX)

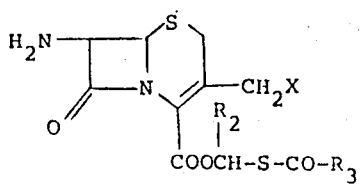

or a salt thereof with a reactive derivative of the acid $R_1$—COOH. Such derivatives include, for example, acid halides, acid anhydrides, mixed anhydrides of the acid with, for example, carboxylic acid monoesters, trimethylacetic acid or benzoic acid, acid azides, active esters such as cyanomethyl ester or p-nitrophenyl ester or active amides such as acylimidazoles.

The acid $R_1$—COOH may also be reacted with a compound of formula IX in the presence of a carbodiimide, for example, N,N'-dicyclohexylcarbodiimide, or an isoxazole salt such as N-ethyl-5-phenylisoxazolium-3'-sulfonate, or 2-ethoxy-1,2-dihydroquinoline-1-carboxylic acid ethyl ester.

The compounds of formula IX are also new, and may be produced, for example, by the reaction of a compound of the formula (X)

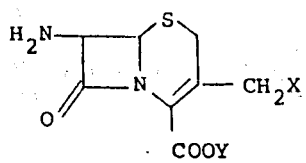

with a compound of formula V above. This reaction is effected at a temperature within the range of about 0° to 50°C., preferably about room temperature, in an inert solvent such as dimethylformamide.

The compounds of formula IX may also be produced from compounds of formula I, especially when $R_1$ is a selected substituent such as benzyl or phenoxymethyl, by converting this particular compound of formula I with phosphorus pentachloride under anhydrous conditions to an imide chloride of the formula (XI)

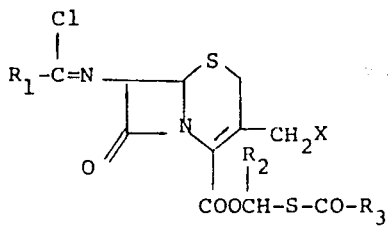

Then, by treating the product of formula XI with certain alcohols, e.g., methanol or isopropanol, and further with water, the product of formula IX optimally in the form of its salt, such as the hydrochloride or tosylate, is obtained. By forming the salt the molecule is stabilized and more readily isolated.

Further process details are also provided in the illustrative examples.

Certain of the compounds of this invention may exist in different optically active forms. The various stereoisomeric forms as well as the racemic mixtures are within the scope of the invention.

The compounds of this invention have antibacterial activity against both gram positive and gram negative organisms such as *Staphylococcus aureus, Salmonella schottmuelleri, Pseudomonas aeruginosa, Proteus vulgaris, Escherichia coli* and *Streptococcus pyogenes*. They may be used as antibacterial agents in a prophylactic manner, e.g., in cleaning or disinfecting compositions, or otherwise to combat infections due to organisms such as those named above. They also show activity against fungi like *Candida albicans*. For example, a compound of formula I or a physiologically acceptable salt thereof may be used in various animal species in an amount of about 3 to 100 mg./kg., daily, orally or parenterally, preferably orally, in single or two to four divided doses to treat infections of bacterial origin, e.g., 4.0 mg./kg. in mice.

Up to about 500 mg. of a compound of formula I or a physiologically acceptable salt thereof may be incorporated in an oral dosage form such as tablets, capsules or elixirs or in an injectable form in a sterile aqueous vehicle prepared according to conventional pharmaceutical practice.

They may also be used in cleaning or disinfecting compositions, e.g., for cleaning barns or dairy equipment, at a concentration of about 0.01 to 0.5% by weight of such compounds admixed with, suspended or dissolved in conventional inert dry or aqueous carriers for application by washing or spraying. They are also useful as nutritional supplements in animal feeds.

The following examples are illustrative of the invention. All temperatures are on the centigrade scale. Additional variations may be produced in the same manner by appropriate substitution in the starting material.

EXAMPLE 1

21.4 g. (0.05 mol.) of the potassium salt of 7-(phenylacetamido)cephalosporanic acid, 8.45 g. (0.05 mol.) of (bromomethyl)acetylsulfide and 200 ml. of anhydrous dimethylformamide are stirred for 48 hours at room temperature with the exclusion of moisture. The reaction mixture is poured, with stirring into 1 liter of ice water, treated with ethyl acetate and the aqueous phase is shaken twice more with ethyl acetate. The combined ethyl acetate extracts are washed five times with water, decolorized with activated carbon, dried with magnesium sulfate and the solvent then driven off in vacuo in a rotary evaporator. The crude yield is 21.2 g. of a viscous syrup.

The crude product is purified by dissolving the methylene chloride and the solution is chromatographed in a silica gel column. The product is eluted from the column with a mixture comprising 2 parts of methylene chloride and 1 part tetrahydrofuran. After concentrating, there are obtained 12.8 g. of residue, which solidifies upon trituration with ether. The product thus ob- The following additional products are made by the procedure of Example 1 by substituting for the bromomethylsulfide the appropriately substituted sulfide.

tained, the (acetylthio)methyl ester of 7-(phenylacetamido)cephalosporanic acid, melts at 95°–100°.

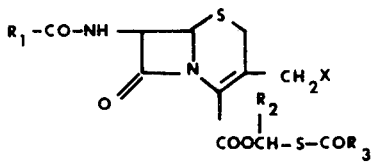

| Ex. | R₁ | R₂ | R₃ | X |
|-----|----|----|----|---|
| 2 | HO—C₆H₄—CH(NH₂)— | CH₃ | —CH₂CH₃ | H |
| 3 | 3,5-Cl₂-4-HO—C₆H₂—CH(NH₂)— | H | —C₆H₄—Cl | —OCOCH₃ |
| 4 | Cl—C₆H₄—CH(NH₂)— | —C₆H₅ | —CH₃ | —OCOC₂H₅ |
| 5 | CH₃O—C₆H₄—CH(NH₂)— | —CH₂CH₃ | —CH₃ | —OCO—C₆H₅ |
| 6 | NH₂—C₆H₄—CH₂— | —CH₂—C₆H₅ | —CH₃ | H |
| 7 | C₆H₅—CH(NH₂)— | H | —CH₂—C₆H₅ | —OCO—CH₂—C₆H₅ |
| 8 | C₆H₅—CH(NH—CO—NH₂)— | H | —C(CH₃)₃ | —SCH₃ |
| 9 | C₆H₅—CH(NH—CO—NH—COCH₃)— | —CH₃ | —C₆H₅ | H |
| 10 | C₆H₅—CH(NH—CO—NH—SO₂—C₆H₅)— | H | —CH₃ | —OCOCH₃ |
| 11 | C₆H₅—CH(OH)— | H | —C(CH₃)₃ | OCH₃ |
| 12 | C₆H₅—CH(COOH)— | —C₆H₅ | —CH₃ | H |

-continued

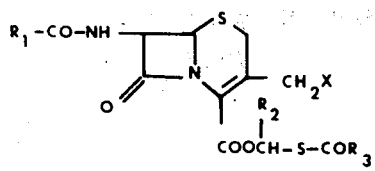

| Ex. | R₁ | R₂ | R₃ | X |
|---|---|---|---|---|
| 13 | C₆H₅-CH(SO₃H)- | H | -CH₂CH₃ | -OCOC₂H₅ |
| 14 | 2-thienyl-CH₂- | H | -CH₃ | -OCOC₆H₅ |
| 15 | 2-furyl-CH₂- | -CH₂CH₂C₆H₅ | -CH₃ | -OH |
| 16 | 2-thienyl-CH(NH₂)- | H | -C(CH₃)₃ | -SCH₃ |
| 17 | 2-thienyl-CH(NH₂)- | -CH₃ | -CH₂-CH(CH₃)₂ | -OCH₃ |
| 18 | C₂H₅ | H | -CH₃ | piperidinium (N⁺) |
| 19 | C₃H₇ | CH₃ | -CH₂CH=CH₂ | H |
| 20 | 2-thienyl-CH₂- | H | -C₆H₅ | -OCOCH₃ |
| 21 | 2-thiacyclohexyl-CH₂- | H | CH₃ | -OCH₃ |
| 22 | cyclohexyl-CH₂- | H | CH₃ | H |
| 23 | C₆H₅-CH(NH₂)- | H | CH₃ | H |
| 24 | 5-methylisoxazol-4-yl-CH₂- | H | CH₃ | H |
| 25 | C₆H₅-O-CH₂- | CH₃ | CH₃ | -S-(5-methyl-1,3,4-oxadiazol-2-yl) |
| 26 | C₆H₅-CH₂- | H | C₂H₅ | -S-(1,3,4-thiadiazol-2-yl) |

-continued
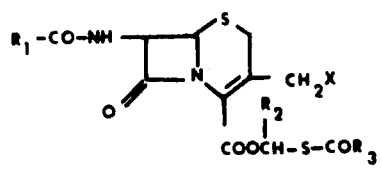
| Ex. | R₁ | R₂ | R₃ | X |
|---|---|---|---|---|
| 27 | 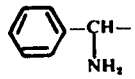 | H | CH₃ | 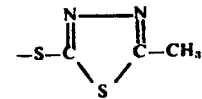 |
| 28 | NC—CH₂— | CH₃ | 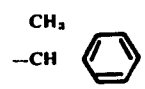 | H |
| 29 | 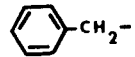 | C₂H₅ | 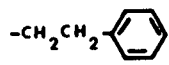 | —OCOCH₃ |
| 30 | 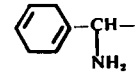 | C₂H₅ | —CH(C₆H₅)₂ | H |
| 31 | N₃—CH₂— | H |  | —OCOCH₃ |
| 32 | 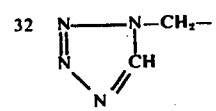 | H | | H |
| 33 | 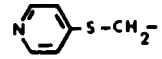 | H | —CH₂CH₂CH₃ | —SCH₃ |
| 34 | 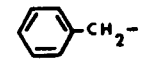 | H | —C(C₆H₅)₃ | H |
| 35 | 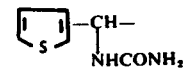 | CH₃ | CH₃ | H |
| 36 | 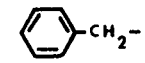 | H | CH₃ | H |
| 37 | 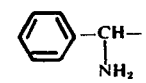 | H | CH₃ | H |
| 38 |  | H |  | H |
| 39 | 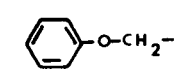 | H | CH₃ | OCOCH₃ |

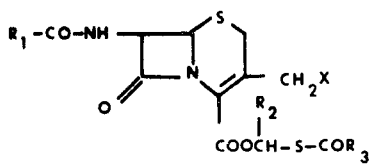

| Ex. | $R_1$ | $R_2$ | $R_3$ | X |
|---|---|---|---|---|
| 40 | (thienyl)-CH(COOH)- | H | $CH_3$ | H |
| 41 | (thienyl)-CH(OH)- | $CH_3$ | $CH_3$ | —$OCOCH_3$ |
| 42 | (pyridyl)-S-$CH_2$- | $CH_3$ | H | H |
| 43 | (phenyl)-CH($NH_2$)- | H | $CH_3$ | —S—(1-methyl-tetrazol-5-yl) |
| 44 | (phenyl)-CH($NH_2$)- | $CH_3$ | $C_2H_5$ | —S—(1H-tetrazol-5-yl) |
| 45 | (phenyl)-CH($NH_2$)- | H | $CH_3$ | —S—(1H-tetrazol-5-yl) |

What is claimed is:

1. A compound of the formula

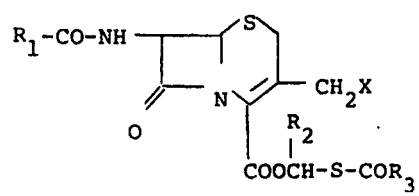

wherein $R_1$ is α-aminobenzyl; $R_2$ is hydrogen or lower alkyl; $R_3$ is lower alkyl; and X is tetrazolylthio or (lower alkyl)-tetrazolylthio.

2. A compound as in claim 1 wherein $R_1$ is α-aminobenzyl and $R_2$ is hydrogen.

3. A compound as in claim 2 wherein X is tetrazolylthio.

4. A compound as in claim 2 wherein X is (lower alkyl)tetrazolylthio.

5. A compound as in claim 2 wherein $R_3$ is methyl and X is (1-methyl-1H-tetrazol-5-yl)thio.

6. A compound as in claim 2 wherein $R_3$ is methyl and X is 1H-tetrazol-5-yl.

* * * * *